US006650944B2

(12) United States Patent
Goedeke et al.

(10) Patent No.: US 6,650,944 B2
(45) Date of Patent: Nov. 18, 2003

(54) FOLLOW-UP MONITORING METHOD AND SYSTEM FOR IMPLANTABLE MEDICAL DEVICES

(75) Inventors: Steven D. Goedeke, Forest Lake, MN (US); David L. Thompson, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 356 days.

(21) Appl. No.: 09/732,951

(22) Filed: Dec. 8, 2000

(65) Prior Publication Data

US 2002/0072783 A1 Jun. 13, 2002

Related U.S. Application Data

(60) Provisional application No. 60/184,221, filed on Feb. 23, 2000.

(51) Int. Cl.[7] ................................................. A61N 1/08

(52) U.S. Cl. ............................. 607/60; 607/57; 607/32; 128/903

(58) Field of Search ........................... 128/903; 607/60, 607/57, 32, 30

(56) References Cited

U.S. PATENT DOCUMENTS

| | | | |
|---|---|---|---|
| 2,027,898 A | 1/1936 | Broulhiet | 280/106 |
| 4,825,869 A | 5/1989 | Sasmor et al. | 128/419 PT |
| 5,113,869 A | 5/1992 | Nappholz et al. | 128/696 |
| 5,336,245 A | 8/1994 | Adams | 607/32 |
| 5,354,319 A * | 10/1994 | Wyborny et al. | 607/32 |
| 5,381,798 A | 1/1995 | Burrows | 128/696 |
| 5,383,915 A | 1/1995 | Adams | 607/60 |
| 5,511,553 A | 4/1996 | Segalowitz | 128/696 |
| 5,564,429 A | 10/1996 | Bornn | 128/696 |
| 5,617,871 A | 4/1997 | Burrows | 128/696 |
| 5,626,151 A | 5/1997 | Linden | 128/897 |
| 5,626,630 A | 5/1997 | Markowitz et al. | 607/60 |
| 5,683,432 A | 11/1997 | Goedeke et al. | 607/32 |
| 5,690,690 A * | 11/1997 | Nappholz et al. | 607/30 |
| 5,748,103 A | 5/1998 | Flach et al. | 340/870.07 |
| 5,752,976 A | 5/1998 | Duffin et al. | 607/32 |
| 5,752,977 A | 5/1998 | Grevious et al. | 607/32 |
| 5,759,199 A | 6/1998 | Snell et al. | 607/60 |
| 5,792,207 A | 8/1998 | Dietrich | 607/32 |
| 5,833,623 A | 11/1998 | Mann et al. | 600/523 |
| 5,836,989 A | 11/1998 | Shelton | 607/27 |
| 5,843,139 A | 12/1998 | Goedeke et al. | 607/32 |
| 5,891,178 A | 4/1999 | Mann et al. | 607/27 |

(List continued on next page.)

OTHER PUBLICATIONS

Bernard, Stan, M. "Online Outpatients," Business 2.0, Jan. 1, 2000 issue. 3pp.

*Primary Examiner*—Gene Mancene
*Assistant Examiner*—Frederick C. Nicolas
(74) *Attorney, Agent, or Firm*—Girma Wolde-Michael; Daniel G. Chapik

(57) ABSTRACT

A method and a system for retrieving information from an IMD so that a physician may better use the time allotted to a patient. In an example embodiment, a method for communicating between an implanted device and a medical data processing system occurs via a communications module coupled to an antenna member and to the medical data processing system. The communication module and the antenna are arranged to transmit and receive radio frequency signals within a given range or space such as in a room. The method includes broadcasting interrogation requests in the range via the communications module and antenna arrangement and establishing a communications link between the implanted device present in the range and the communications module. A set of patient diagnostic data is then transmitted from the implanted device to the communications module in response to an encoded radio frequency signal from the communications module. The set of diagnostic data is then processed and reported via the medical data processing system for use during a patient examination.

32 Claims, 3 Drawing Sheets

U.S. PATENT DOCUMENTS

| | | | |
|---|---|---|---|
| 5,935,078 A | * 8/1999 | Feierbach | 600/509 |
| 6,057,758 A | 5/2000 | Dempsey et al. | 340/539 |
| 6,083,248 A | 7/2000 | Thompson | 607/30 |
| 6,160,478 A | * 12/2000 | Jacobsen et al. | 340/539 |
| 6,201,993 B1 | * 3/2001 | Kruse et al. | 607/30 |
| 6,301,504 B1 | * 10/2001 | Silvian | 607/60 |
| 6,308,099 B1 | * 10/2001 | Fox et al. | 607/31 |
| 6,400,990 B1 | * 6/2002 | Silvian | 607/60 |
| 6,442,433 B1 | * 8/2002 | Linberg | 607/60 |
| 6,443,891 B1 | * 9/2002 | Grevious | 600/302 |
| 2002/0023654 A1 | * 2/2002 | Webb | 128/899 |

\* cited by examiner

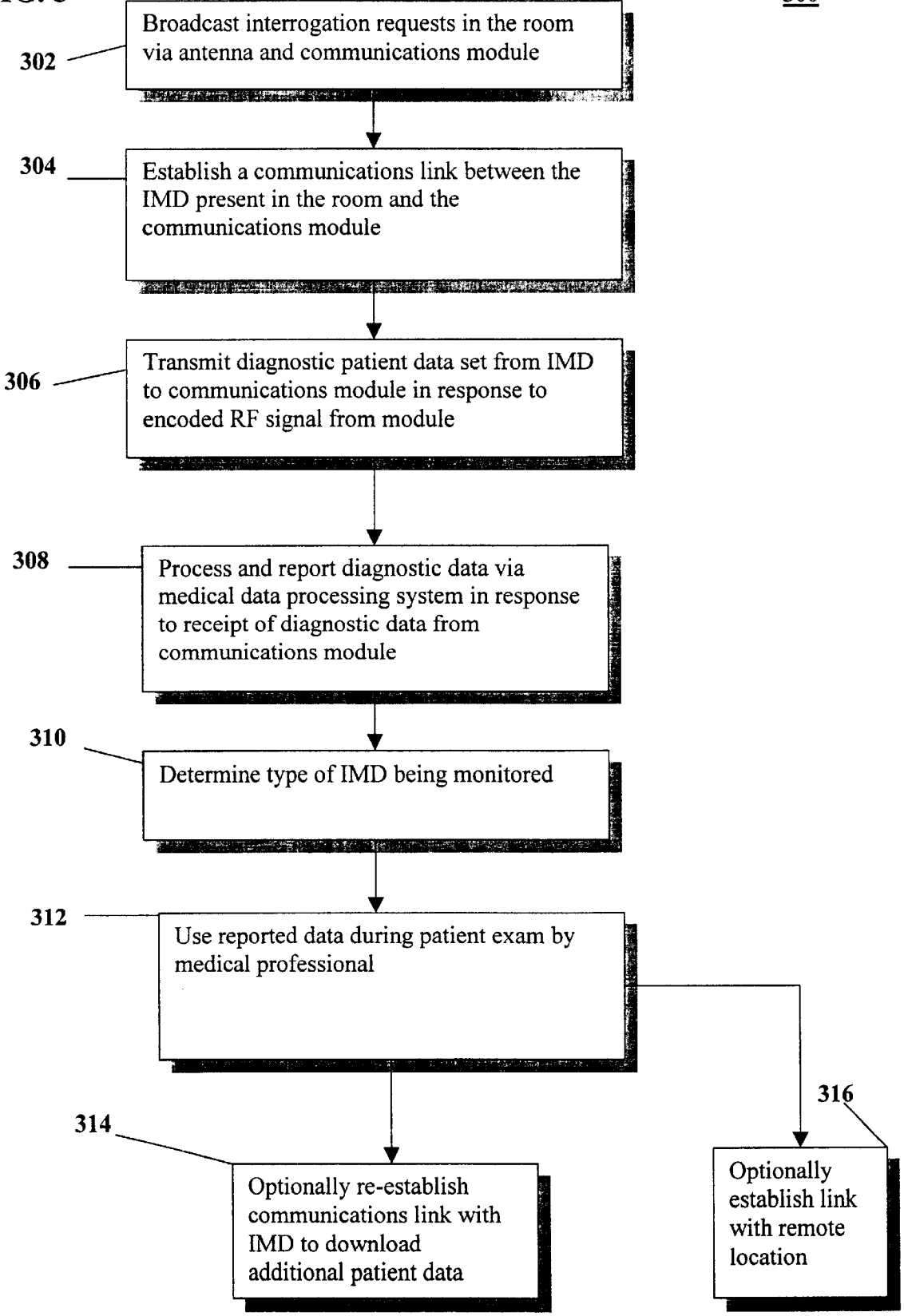

FOLLOW-UP MONITORING METHOD AND SYSTEM FOR IMPLANTABLE MEDICAL DEVICES

RELATED PATENT DOCUMENTS

This application claims priority to U.S. Provisional Application Ser. No. 60/184,221, filed on Feb. 23, 2000 (P-8496.00), entitled "Follow-up Monitor for Implantable Medical Devices." The disclosure and drawings of the Provisional application are specifically incorporated herein by reference.

FIELD OF THE INVENTION

The present invention generally relates to implantable medical devices and instruments. Specifically, the invention relates to a method and a system for collecting diagnostic data from an implantable medical device (IMD) using a telemetry scheme.

BACKGROUND OF THE INVENTION

In recent years, implantable medical device technology has rapidly advanced. Sizes and weights of devices have decreased, while functionality has increased. These advances have created a corresponding demand for improved two-way communication or telemetry between the implantable medical device and an external device, for example, a programmer device. In a pacemaker system, for example, a programmer device downloads to an implanted pacemaker, data such as operating parameters. Likewise, data may flow from the implanted device to the programmer device. Modem pacemakers are capable of storing significant amounts of data about the patient, for example, the average heart rate, and information pertaining to the pacemaker itself, for example, battery voltage level. Generally, the implanted device is transmitted to the programmer device for review and evaluation by a physician.

Current programming devices typically include an extendible head portion that includes an antenna. The antenna is connected to other circuitry in the programmer device via a stretchable coil cable. Thus, the head portion can be positioned over the patient's implanted device site for programming or telemetry interrogation of the implanted device. Command instructions or data that are downloaded to the implanted device are referred to as downlink transmissions, and data transmitted from the implanted device to the programmer device are referred to as uplink transmissions.

Patients with IMDs, such as a pacemaker or a defibrillator, are normally required to visit their physician on a regular schedule. These visits usually involve the physician reviewing diagnostic data retrieved by interrogation of the IMD. The retrieved data includes, for example, a device ID, patient identification information, device status, diagnostic counters, trend information, and stored IEGM (intracardiac electrogram).

Cost containment requirements of hospitals and clinics are forcing physicians to examine more patients in less time. As a result, the average physician no longer has the freedom to have open-ended visits with patients and must now allot a limited amount of consultation time per patient.

The reduced time that physicians have for examining patients is especially impacting patients using IMDs. Based on current data transmission techniques for IMDs, the uplink transmission time may take as long as 15 minutes for approximately 256 Kbytes and in the future could easily increase to over 60 minutes for approximately 1 Mbyte. Although future telemetry systems may provide increased bandwidth, the continued increase in data being stored within implantable devices may offset this advance.

SUMMARY OF THE INVENTION

Various embodiments of the present invention are directed to addressing the above and other needs in connection with conducting external follow-up monitoring of IMDs while patients are waiting in a hospital or clinic waiting room prior to a routine or emergency meeting with their physician. More specifically, the invention enables the collection of diagnostic data from IMDs while patients are waiting to be examined, thereby improving physician efficiency and reducing medical costs. Accordingly, it has been discovered that reducing the time required to retrieve information from an IMD provides the physician with the opportunity to better use the time allotted for each patient.

According to one embodiment of the invention, a method for communicating between an implanted device and a medical data processing system occurs via a communications module coupled to an antenna member and to the medical data processing system. The communication module and the antenna are arranged to transmit and receive radio frequency signals within a range. The method includes broadcasting interrogation requests in the range via the communications module and antenna arrangement and establishing a communications link between the implanted device present in the range and the communications module. A set of patient diagnostic data is then transmitted from the implanted device to the communications module in response to an encoded radio frequency signal from the communications module. In response to receiving the transmitted set of diagnostic data from the communications module, processing and reporting the set of diagnostic data commences via the medical data processing system. The reported set of diagnostic data is then used by the medical professional, for example, during a patient examination.

According to another embodiment of the invention, a system for communicating between an implanted device and a medical data processing system includes a data processing system configured and arranged to generate a control signal to initiate communication with an implanted medical device and an antenna arrangement that is coupled to a communications module located in at least one range that is configured and arranged to transmit radio frequency signals recognizable by the implanted device. The communication module is configured and arranged to establish a communications link between the implanted device present in the range and the medical data processing system. In addition, the communications module is configured and arranged to automatically retrieve a set of diagnostic patient data from the implanted device after the implanted device has responded to an encoded radio frequency signal sent by the medical data processing system. The medical data processing system is configured to process and report the set of patient data for use during a patient examination.

The above summary of the present invention is not intended to describe each illustrated embodiment or every implementation of the present invention. The figures in the detailed description that follow more particularly exemplify these embodiments.

BRIEF DESCRIPTION OF THE DRAWINGS

The invention may be more completely understood in consideration of the following detailed description of various embodiments of the invention in connection with the accompanying drawings, in which:

FIG. 3 is a flowchart illustrating the manner of communicating with an IMD and processing diagnostic data for patient evaluation in accordance with an example embodiment of the invention.

Figure 1:
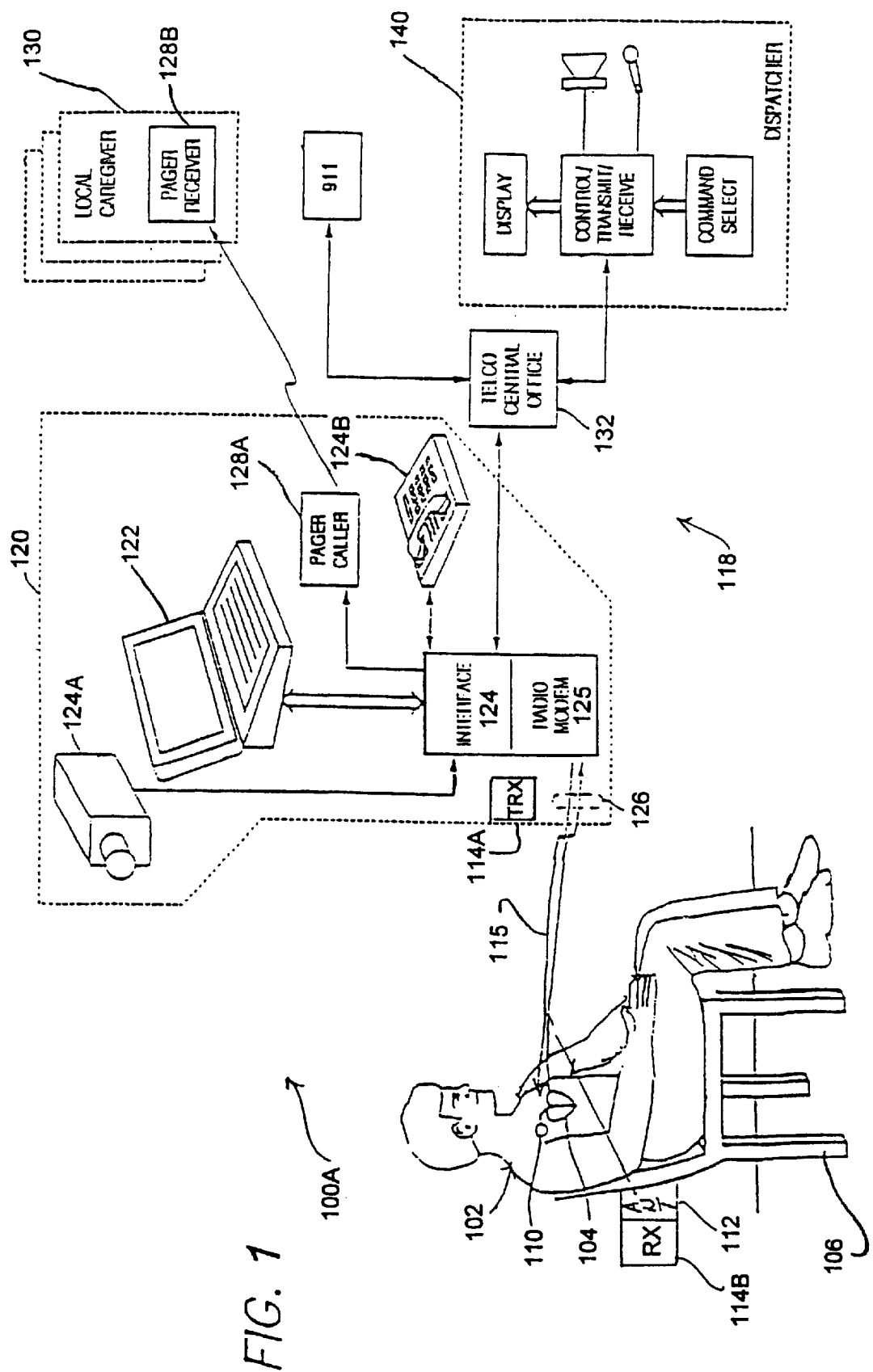
FIG. 1 illustrates a diagram of an implanted medical device communications system in accordance with an example embodiment of the invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

The present invention is generally directed to a method and system for uplinking and retrieving information from one or more IMDs, prior to consultation with a physician, in order to reduce the time and cost associated with a visit to a physician. While the present invention is not necessarily limited to such an application, the invention will be better appreciated using a discussion of example embodiments in such a specific context.

In an example embodiment, a patient's IMD diagnostic data is retrieved via an uplink to a programmer device while, for example, that patient is waiting prior to an examination. An uplink transmission with the IMD is established using an antenna and transceiver arrangement located in a designated area, such as a waiting or examination range. Upon patient check-in, IMD interrogation and collection of all patient diagnostic data is performed prior to consultation with the physician. The patient diagnostic data can then be processed before or during consultation with the physician. In one embodiment, the patient may move freely in the range while the IMD is being interrogated. In other embodiments, multiple antenna arrangements could be located in the designated area using known time multiplexing or code-based sharing of a carrier frequency to enable extensive reach and allow patient mobility.

Referring now to the figures, FIG. 1 illustrates an implantable medical device communications and interrogation system 100A in accordance with an example embodiment of the present invention. Communications and interrogation system 100A includes at least one IMD 110, implanted within a patient 102 and coupled to the patient's heart 104, that communicates with an antenna 126 that forms part of a communications system 118. Antenna 126 is coupled to either a transceiver 114A or to a radio modem 125. In an example embodiment, transceiver 114A in a simpler format is substitutable for a transmitter or a receiver.

In this example embodiment, communications system 118 is comprised of a medical communications system 120 and remote communications modules 130 and 140 that are communicatively coupled to system 120. Medical communications system 120 includes a medical data processing system or diagnostic equipment 122 that is capable of processing information collected from IMD 110 via a communications link 115. The medical data processing system is configured to process and report patient diagnostic data retrieved from the IMD before a medical professional examines the patient. Remote communications module 130, in this example, includes a remotely located physician or caregiver center 130 that permit physicians or expert data centers to communicate remotely with the patient's IMD 110. Module 140, on the other hand, includes an emergency dispatch system that requests emergency personnel when the patient is experiencing a critical problem with the IMD.

In an example embodiment, IMD 110 communicates with an antenna 112 coupled to a transceiver unit 114B that is mountable on a chair 106 in which patient 102 is sitting. Communications system 118 is then communicatively coupled to transceiver unit 114B via communications link 115. In this example, link 115 includes a cabling system, an RF wireless link, an infrared link, an optical link or any other means that permits one and two way communications between transceiver unit 114B and medical communications system 120. In this example, a patient with one or more implanted medical devices sits in a chair 106 that either has the antenna 112 and transceiver 114B combination affixed thereto, or has the combination removably mounted to the back of the chair at about the time the patient is going to sit down. This example embodiment is not limited to seating arrangements and includes furniture (e.g., couches, benches, disabled personnel seats, and counters), mobile systems (ambulances, vehicles, ships and airplanes) that can accommodate antenna 112 and transceiver unit 114B. The antenna and transceiver combination forms a small telemetry zone or link (not shown) that emanates through the body of patient 102. The telemetry zone establishes communications between the patient's IMD 110 and the remotely located diagnostic system 122. Diagnostic system 122 is located, in this example, at a nurse's station away from the waiting room.

Transceiver unit 114A is adapted to transmit encoded radio frequency signals, that will be described in further detail with respect to FIG. 2, that are recognizable by IMD 110. Antenna 126 and transceiver unit 114A proceed to establish the communications link between IMD 110 and communications system 118. Once signals or data are received from IMD 110 by antenna 126 the data is transmitted back through the radio modem 125 and through a communications interface 124. Communications interface 124 transmits diagnostic data back to diagnostic system 122 or back to remote module 130 via a pager calling 128A and receiving system 128B. A video camera 124A or a telephone 124B is optionally coupled to interface 124 for additional communications capabilities. Further, remote module 140 is optionally coupled to interface 124 via a central office switching equipment 132 for pre-emptive responses to emergencies.

Figure 2:
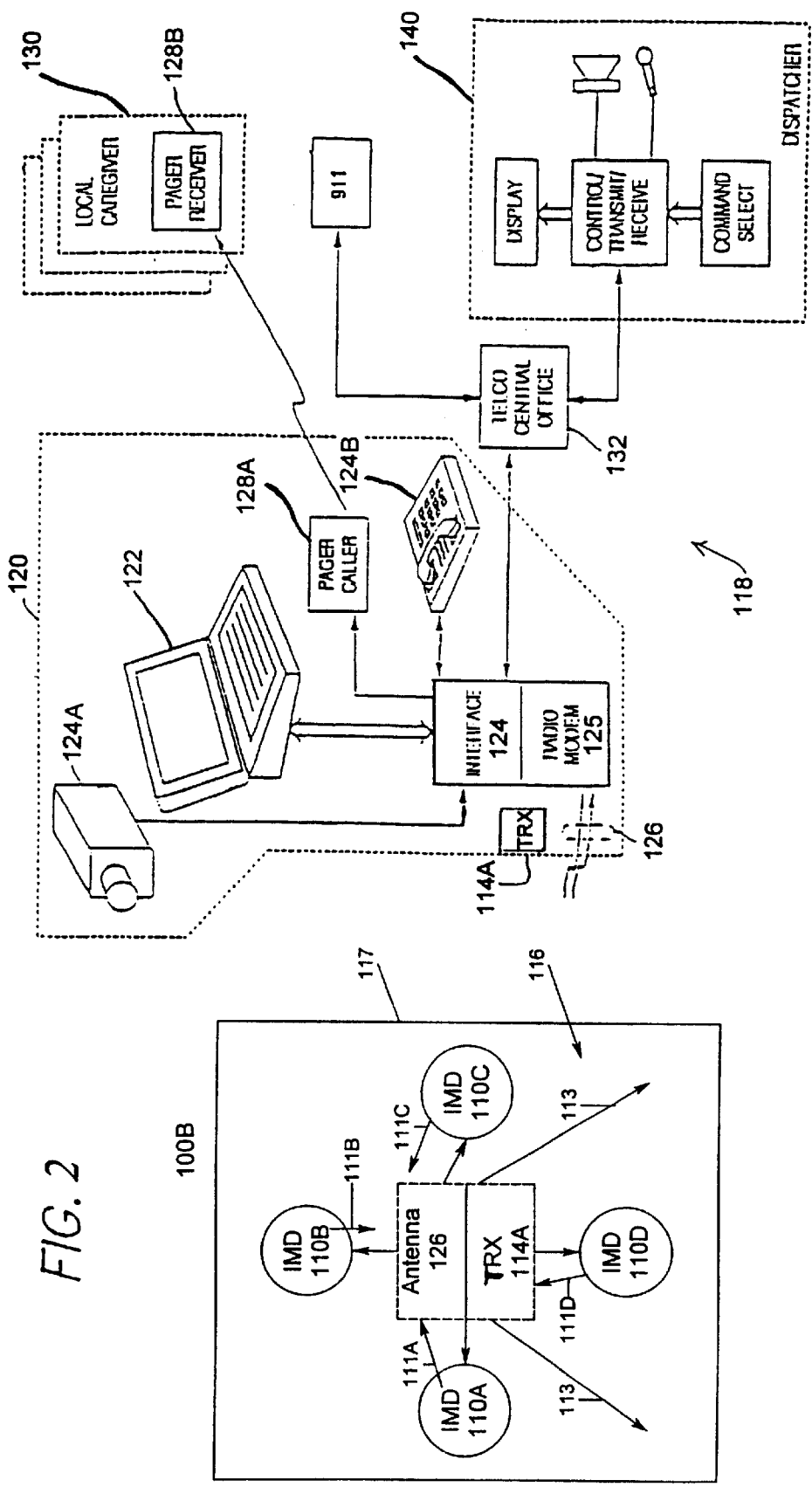
FIG. 2 illustrates a diagram of an implanted medical device communications system in accordance with another example embodiment of the invention.

Referring now to FIG. 2, an alternative embodiment of the implanted medical device communications and interrogation system 100B for interrogating multiple IMDs 110A–110D is illustrated. In this embodiment, system 100B has antenna 126 placed in a designated area (e.g. a waiting or examining room) so as to be in range of the various IMDs 110A–110D. In another embodiment, the antenna is placed high enough to have a clear trajectory to the IMDs; several antennas can also be positioned in the designated area to increase signal coverage and expand the designated area. Antenna 126 is coupled to the radio modem 125 or to a transceiver unit 114A that is coupled to interface 124. Interface 124 is coupled to medical data processing system 122 capable of processing information collected from IMDs 110A–110D.

In this example, patients with implanted medical devices walk into a designated area or range 116 that has a telemetry zone 117 established therein via antenna 126 and communications system 118 that includes transceiver 114A. Telemetry zone 117 within range 116 establishes communications between the various patients with IMDs 110A–110D that are present within range 116 (enveloped by zone 117) and the remotely located diagnostic system 122. Diagnostic system 122 is located, in this example, at a nurse's station away from waiting area 116. In this example, transceiver unit 114A transmits encoded radio frequency signals 113 via antenna 126, which are recognizable as interrogation requests by IMDs 110A–110D, in response to diagnostic system 122 commands. Transceiver unit 114A sends or broadcasts downlink command messages via coded radio frequency signals 113 prompting that an uplink transmission is being sought with the various IMDs 110A–110D that are present in, or in close proximity to, telemetry zone 117. In response, IMDs 110A–110D send back radio signals 111A–111D indicating whether or not they are ready to establish the uplink transmission with transceiver 114A and ultimately diagnostic system 122. Block transmissions of data are sent from each IMD within telemetry zone 117 to diagnostic system 122. After each block of data is transmitted, a CRC code is sent with each block to ensure proper transmission. Noise, retransmissions and CRC code transmissions are factors that are known to increase uplink transmission times, thereby illustrating even further the value and importance of interrogating the IMDs prior to the physician's (or IMD operator) involvement. Diagnostic system 122 is capable of verifying the integrity of the transmitted data and then determining if the transmission is complete or if another transmission is necessary due to the receipt of corrupted data.

Diagnostic system 122 is capable of distinguishing between the various IMDs 110A–110D since IMD transmission blocks lead off with the serial number, model number and device status that is unique to each IMD and patient. In an example embodiment, time-based multiplexing and code-based sharing of the carrier frequency is used to collect the data from the various patients during deadtime between transmissions. In another embodiment, diagnostic system 122 via transceiver unit 114A uses various communications channels to communicate with the different IMDs. In the case where the patient has several IMDs, any of the above-described methods are available to distinguish between the data signals coming from the various IMDs within a single patient. A more detailed discussion of the methods of communicating with an IMD is provided in U.S. Pat. No. 5,683,432 to Goedeke et al and in U.S. Pat. No. 5,843,139 to Goedeke et al., which are assigned to the assignee of the present invention and are incorporated herein by reference.

In an example embodiment, the communications and interrogation system invokes remote communications modules 130 and 140 to provide a communications link to networks outside the immediate location of medical diagnostic system 122. Communications links include a local area network, wide area network and a public service telecommunications network via a cellular link or hardwire connection. A link can also be provided to the Internet via a PC or a wireless link to a global satellite communications network. The communications networks that these systems can connect to include a public service telephone network, LAN, a WAN, internal public exchange, wireless, microwave, global satellite communications and the World Wide Web. The remote communications modules are coupled to medical diagnostic system 122 via hardwire (through central office 132 and module 140) or wirelessly, for example, through pager calling system 128A/128B to module 130. A more detailed discussion of the methods of communicating remotely with an IMD is provided in U.S. Pat. No. 5,752,976 to Duffin et al, which is assigned to the assignee of the present invention and is incorporated herein by reference.

In one example embodiment, the communications and interrogation system of the present invention is configured and arranged to transmit the data obtained from the IMD to the antenna and transceiver unit and ultimately to a data center or doctor station. At the data center, a physician or healthcare specialist provides remote analysis of the data and approves changes in therapy or diagnosis. In an example embodiment, the medical or diagnostic systems are programmed to continuously transfer data between an expert data center and the IMD(s). Waiting rooms can also be equipped with alarm systems to notify the patient and the remote physician about critical developments or impending problems based on anomalies in the readings or other physiological data trends. In yet another related application, diagnostic system 122 is configurable to transmit downloading commands via system 118 to the various IMDs for purposes of updating or adjusting the software of the IMDs after interrogation is complete.

Referring now to FIG. 3, a flowchart 300 illustrates the manner of communicating and reporting diagnostic data from an IMD of a patient located in a range prior to a physician's examination in accordance with an example embodiment of the invention. Communications between an IMD and a medical data processing system is performed via a communications module that is coupled to an antenna member, the antenna and the communications module being configured and arranged to transmit and receive radio frequency signals within the range. When the patient checks in at the nurse's station and has his name logged in, an interrogation request can commence at this point. At step 302, the medical communications system (including a medical data processing system) broadcasts interrogation requests within the range 116 via antenna 126 and the communications module (e.g., transceiver 114A). The interrogation requests, in this example embodiment, are continuous, occurring about one every minute. Telemetry zones within an area vary in size, as described in reference to FIGS. 1 and 2, however, the size or extent of coverage can be increased with the use of RF repeaters or by adding additional antennas and receivers to the front end of the communications and interrogation system.

At step 304, a communications link is then established between the IMD present in the range and the communications module. At step 306, upon establishing and confirming the communications link, which can be in the form of a return signal from the IMD, a set of patient diagnostic data is initially transmitted from the IMD to the medical data processing system 122. The diagnostic data is transmitted through the communications system 118 to data processing system 122 in response to a command given to the communications module to transmit an encoded radio frequency (RF) signal that elicits the data transmissions.

At step 308, in response to receiving the transmitted set of diagnostic data from the communications module, the patient data is then processed, formatted for analysis and is reported by medical processing system 122. At step 310, an optional step to processing the patient data includes determining the type of IMD being monitored and the status of the integrity of exchange of data between the IMD and the diagnostic system 122. Initial patient data normally includes data that identifies the type of implanted device (or devices) that is implanted in one patient. The patient data may also identify the types of devices implanted in more than one patient. This information provides the medical data processing system with an initial reference point for selecting and sending commands. At step 312, the reported data is then used by a medical professional, for example, while examining a patient. The reported data may be in the form of a hard copy, paper report or is displayable on a programmer or computer screen. At step 314, the communications link with the IMD can optionally be re-established where a second set of diagnostic patient data is desired or where the original set of data is not satisfactory for patient evaluation purposes. In an example embodiment, re-establishing communications is useful for making adjustments or upgrading the IMD software program. In an example embodiment, a remote communications link is optionally established at step 316 where the data center or doctor station is remotely located and the retrieval of information and post processing analysis is performed before review of the diagnostic data by the physician or IMD operator specialist.

With respect to the present invention, the process of interrogating an IMD is completely invisible to the patient and allows normal patient movement during interrogation. Interrogation and processing status of the IMD is monitorable from a remote location and allows for on-going correction of IMD device anomalies; the re-initiation of interrogation when desirable or necessary, notice of when the interrogation is complete and warning alerts that may be triggered during the interrogation session. Post processing, in this embodiment, consists of formatting data in charts or graph form, searching for anomalous device function or analyzing and formatting non-physiologic data.

Some of the advantages provided by the various embodiments of the present invention include increased flexibility of patient movement without corrupting the data transferred; increased accuracy of data being communicated between the implanted device and the medical communications system. In addition, the present invention provides for a comfortable session between patient and clinician and eliminates the necessity of a lengthy time period in which the programmer must be held in close proximity to the IMD to establish a reliable communications link.

The present invention provides, in an example application, non-invasive clinical data measurements (or control of) various IMDs including but not limited to drug pumps, neurological implants, nerve stimulators, various cardiac implants and equivalent medical devices. The present invention is compatible to a number of techniques for interrogating implantable medical devices. In addition, embodiments described are compatible with remote patient management systems that interact with remote data and expert data centers and compatible with a data communication system that enables the transfer of clinical data from the patient to a remote location for evaluation, analysis, data reposition, and clinical evaluation. For a detailed discussion on the different types of diagnostic data retrievable from an IMD reference is made to U.S. Pat. No. 5,833,623 to Mann et. al; which is incorporated herein by reference. The present invention is compatible with various data mining and network communication systems such as the Internet, Intranet and the World Wide Web.

Various modifications, equivalent processes, as well as numerous structures to which the present invention may be applicable will be readily apparent to those of skill in the art to which the present invention is directed upon review of the present specification. The claims are intended to cover such modifications and devices.

We claim:

1. A method for communicating between an implanted medical device and a medical data processing system, the method comprising:
    broadcasting interrogation requests throughout a non-contact broadcast range;
    establishing a communications link with an implanted medical device within the non-contact broadcast range;
    transmitting a set of diagnostic data from the implanted device in response to a broadcast interrogation request; and
    processing and reporting a transmitted set of diagnostic data at the medical data processing system for use during a patient examination.

2. The method of claim 1, wherein the step of establishing a communications link includes the step of eliciting a response signal from the implanted medical device upon receipt of the encoded signal when the implanted medical device is in the non-contact broadcast range.

3. The method of claim 2, further comprising the step of transmitting data to the implanted medical device for programming the implanted medical device after the step of eliciting a response from the implanted medical device.

4. The method of claim 2, further comprising the step of transmitting data to the implanted medical device for testing the implanted medical device after the step of eliciting a response from the implanted medical device.

5. The method of claim 1, wherein the step of processing and reporting the set of diagnostic data for display includes the steps of formatting the diagnostic data in graphical form and reviewing the diagnostic data for non-physiologic data after receipt of the diagnostic data.

6. The method of claim 5, wherein processing the diagnostic data set includes the step of searching the diagnostic data for an anomalous implanted device function.

7. The method of claim 1, further comprising the step of transmitting the diagnostic data to a location remote from the range for review by a medical professional after the diagnostic data is reported.

8. The method of claim 1, further comprising the step of placing an antenna member coupled to the transceiver unit on a seating arrangement for the patient before broadcasting the interrogation requests.

9. The method of claim 1, further comprising the step of coupling a plurality of antennas to the transceiver unit before broadcasting the interrogation requests.

10. The method of claim 7, wherein transmitting the diagnostic data to the remote location includes the step of transmitting the data from the medical data processing system to a second medical data processing system via a communications network.

11. The method of claim 7, wherein transmitting the diagnostic data to the remote location includes the step of transmitting the data from the medical data processing system to a second medical data processing system via a, wireless communications network.

12. The method of claim 1, wherein the step of processing and reporting the diagnostic data includes the step of distinguishing between a plurality of sets of diagnostic data received from a plurality of implanted medical devices.

13. The method of claim 1, further comprising the step of re-establishing the communications link with the implanted medical device for transmitting a second set of diagnostic data after the step of reporting the diagnostic data.

14. A system for communicating between an implanted medical device and a medical data processing system within a non-contact broadcast range, the system comprising:

means for broadcasting interrogation requests throughout the non-contact broadcast range;

means for establishing a communications link between an implanted medical device within the non-contact broadcast range;

means for transmitting a set of diagnostic patient data from the implanted medical device in response to a broadcast interrogation; and means for processing and reporting a transmitted set of diagnostic data via the medical data processing system for use during a patient examination.

15. The system of claim 14, further comprising an antenna arrangement including a plurality of antenna members placed in the non-contact broadcast range that are coupled to a plurality of transceiver units.

16. The system of claim 14, further including a second medical data processing system remotely located from the broadcast range and coupled to the medical data processing system, the second data processing system being used by a medical professional to evaluate diagnostic data from a patient.

17. The system of claim 14, wherein the medical data processing system receives and distinguishes between a plurality of sets of diagnostic data received from a plurality of implanted medical devices.

18. The system of claim 14, wherein the medical data processing system is configured to mange the diagnostic data in graphical form.

19. The system of claim 14, wherein the medical data processing system is configured to alert a medical professional of detection of an anomalous implanted device function from the diagnostic data.

20. The system of claim 14, wherein the medical data processing system is located remote from the broadcast range and is configured to monitor the data communications with the implanted medical device.

21. The system of claim 14, wherein the implanted medical device is adapted to communicate the diagnostic data in at least one block transmission with a CRC code.

22. The system of claim 14, wherein the medical data processing system is configured to search the diagnostic data for non-physiologic data.

23. The system of claim 14, wherein the medical data processing system is configured to transmit data via an antenna arrangement for programming the implanted medical device.

24. The system of claim 16, wherein the second data processing system and the medical data processing system are coupled via a wireless communications network for the transmission of diagnostic data.

25. A system for interfacing with an implanted medical device, the system comprising:

a data processing system generating a control signal to initiate communication with an implanted medical device in a patient; and a transceiver unit spaced wart from but proximate to the patient and proximate to the data processing system, the transceiver unit generating a first encoded radio frequency signal in response to the data processing system control signal, the encoded radio frequency signal causing an implanted medical device that is proximate to the transceiver unit to generate and transmit a set of diagnostic data as a second encoded radio frequency signal, the transceiver unit further receiving the transmitted set of diagnostic data and sending the data to the data processing system for use during an examination of the patient, wherein communication between the transceiver unit and the implanted medical device can occur when the implanted medical device is anywhere within a telemetry zone that surrounds the whole of the patient's body.

26. The arrangement of claim 25, wherein the data processing system is configured to automatically interrogate at least one implanted medical device tat is proximate to a seating structure, wherein the transceiver unit is attached to the seating structure.

27. The arrangement of claim 25, further including an antenna member arranged to communicate with the transceiver unit and the data processing system.

28. The arrangement of claim 27, further comprising a second data processing system remotely located, the second data processing system being used by a medical professional to evaluate diagnostic data from a patient.

29. The arrangement of claim 28, wherein the remotely located second data processing system and the data processing system are coupled via a wireless communications network for the transmission of diagnostic data.

30. The arrangement of claim 25, wherein the data processing system is configured to receive and distinguish between diagnostic data sets received from a plurality of implanted medical devices.

31. The arrangement of claim 25, wherein the data processing system is configured to arrange the diagnostic data in graphical form.

32. The arrangement of claim 25, wherein the data processing system is configured to search the diagnostic data for an anomalous implanted device function.

\* \* \* \* \*

UNITED STATES PATENT AND TRADEMARK OFFICE
CERTIFICATE OF CORRECTION

PATENT NO. : 6,650,944 B2
DATED : November 18, 2003
INVENTOR(S) : Steven D. Goedeke et al.

It is certified that error appears in the above-identified patent and that said Letters Patent is hereby corrected as shown below:

Column 8,
Line 55, delete "via a," and insert -- via a --.

Column 10,
Line 6, delete "spaced wart", and insert -- spaced apart --.
Line 25, delete "device tat", and insert -- device that --.

Signed and Sealed this

Fourth Day of January, 2005

JON W. DUDAS
*Director of the United States Patent and Trademark Office*